(12) United States Patent
Noda

(10) Patent No.: US 6,669,711 B1
(45) Date of Patent: Dec. 30, 2003

(54) OPERATION BALLOON

(75) Inventor: Kazuhiro Noda, Ikeda (JP)

(73) Assignee: Koken Co. Ltd., Tokyo (JP)

( * ) Notice: Subject to any disclaimer, the term of this patent is extended or adjusted under 35 U.S.C. 154(b) by 0 days.

(21) Appl. No.: 09/762,697

(22) PCT Filed: Aug. 11, 1999

(86) PCT No.: PCT/JP99/04362

§ 371 (c)(1),
(2), (4) Date: Feb. 12, 2001

(87) PCT Pub. No.: WO00/09192

PCT Pub. Date: Feb. 24, 2000

(30) Foreign Application Priority Data

Aug. 17, 1998 (JP) .......................... 10-267204

(51) Int. Cl.[7] .............................................. A61M 29/02
(52) U.S. Cl. ....................................... 606/196; 604/907
(58) Field of Search ................................ 606/192, 196, 606/197, 199, 191, 194, 198, 195; 604/907, 101.01, 101.02, 101.04, 101.05, 919

(56) References Cited

U.S. PATENT DOCUMENTS

| | | | | |
|---|---|---|---|---|
| 1,690,995 A | * | 11/1928 | Pratt ........................... | 606/192 |
| 2,493,326 A | * | 1/1950 | Trinder ....................... | 606/196 |
| 3,570,494 A | * | 3/1971 | Gottschalk .................. | 606/196 |
| 3,766,924 A | * | 10/1973 | Pidgeon ....................... | 606/196 |
| 4,606,346 A | * | 8/1986 | Berg et al. ................... | 606/196 |
| 4,986,815 A | | 1/1991 | Schneider | |
| 5,024,658 A | * | 6/1991 | Kozlov et al. ............ | 604/101.04 |
| 5,071,406 A | * | 12/1991 | Jang ........................ | 604/101.01 |
| 5,139,510 A | * | 8/1992 | Goldsmith et al. ......... | 606/196 |
| 5,413,557 A | | 5/1995 | Solar | |
| 5,454,817 A | * | 10/1995 | Katz ........................... | 606/106 |
| 5,501,667 A | * | 3/1996 | Verduin, Jr. ................. | 606/194 |
| 5,546,964 A | * | 8/1996 | Stangerup .................... | 606/196 |
| 5,588,965 A | | 12/1996 | Burton et al. | |
| 5,797,948 A | * | 8/1998 | Dunham ..................... | 606/194 |
| 6,126,634 A | * | 10/2000 | Bagaoisan et al. .......... | 606/191 |

FOREIGN PATENT DOCUMENTS

| | | |
|---|---|---|
| JP | 63177868 | 7/1988 |
| JP | 3504935 | 10/1991 |
| JP | 3251259 | 11/1991 |
| JP | 461549 | 5/1992 |
| JP | 9501852 | 2/1997 |
| JP | 10506038 | 6/1998 |
| JP | 10337332 | 12/1998 |

\* cited by examiner

*Primary Examiner*—A. Vanatta
(74) *Attorney, Agent, or Firm*—Sherman & Shalloway

(57) ABSTRACT

A surgical balloon which is provided with a plurality of balloons so that a fixing property and a shielding property are simultaneously satisfied, and prevents a liquid or a gas from flowing from one area in the body to another area thereof. The surgical balloon is further provided with a balloon fixing device, a drain for draining water from the front nostril and a tube for supplying rinsing water into the nasal cavity so that a surgical operation using an endoscope is carried out inside the nasal cavity with the nasal cavity filled with a water flow. A high-pressure balloon having a fixing property and a low-pressure balloon having a shielding property are combined, and the balloon is pulled from the periphery of the front nostril so as to be secured; thus, a large amount of water supply and water drain are carried out through the front nostril. Therefore, it is possible to carry out a nose surgical operation using an endoscope in a water flowing, a strong rinsing operation after the surgical operation and a diagnosis inside the nasal cavity using a ultrasonic wave.

9 Claims, 11 Drawing Sheets

2、3、11、12

OPERATION BALLOON

FIELD OF THE INVENTION

The present invention relates to an operation balloon which prevents a liquid or a gas from leaking from one area of the body to another area thereof. More specifically, the present invention concerns a surgical balloon which is constituted by an aggregate of balloons so as to exert a strong shielding force and can close the rear-nasal cavity virtually completely, and which is provided with: a surgical balloon fixing device for pulling the balloon from the front-nasal cavity so as to fix it therein, a nasal drain for draining water from the front-nasal cavity, a soft nasal water-supplying tube for sending rinsing water into the nasal cavity, and a movable nasal water-supplying tube for sending rinsing water into the nasal cavity. This arrangement makes it possible to carry out a surgical operation on the nasal cavity using an endoscope with the nasal cavity filled with a water flow and also to forcefully rinse the nasal cavity after the surgical operation, and also makes it possible to carry out a ultrasonic diagnosis inside the nasal cavity by filling the nasal cavity with a water flow; thus it becomes possible to completely stop bleeding after the nasal surgical operation so that the patient is allowed to leave the hospital earlier, and also to easily stop bleeding even in the case of a patient with serious nose bleeding.

BACKGROUND OF THE INVENTION

In recent years, surgical operations using endoscopes have been widely carried out in various medical fields, and its major advantage is that it is possible to obtain information with detailed views with a minimum of surgical damages. With respect to the sub-nasal cavity surgery, instead of the conventional direct surgery on the sub-nasal cavity accompanying great surgical damages, the surgical operation using a nose endoscope has come to be widely carried out.

Conventionally, in the case of a nose surgical operation using an endoscope, the viewing field of the endoscope tends to become foggy, when even a slight amount of blood or stain adheres to the tip of the endoscope or when the patient's inhaled air passes through the nasal cavity, and every time such a situation occurs, the endoscope has to be pulled out so as to wipe the tip thereof; this causes a serious problem of inefficiency. Moreover, in most cases, the endoscope is held by one hand, and the surgical operation is carried out by the other hand, and in the case of much bleeding, immediately after having removed blood by using a suction tube, etc., the suction tube is taken out, and after switching this to forceps, etc., the forceps have to be inserted to the surgical viewing field; this also causes a serious problem of inefficiency. If the surgical operation is simultaneously carried out while removing blood, a fast operation can be carried out; however, it is very difficult to simultaneously insert the endoscope, the forceps and the suction tube into the narrow front nostril and to operate these.

Conventionally, since bleeding inside the nasal cavity during the operation tends to flow into the throat heads, the patient tends to feel pain, and might have a swallowing action erroneously.

Moreover, conventionally, in the case when a rinsing process is carried out inside the nasal cavity after the operation, since the rinsing liquid flows from the nasal cavity into the throat heads, it has been impossible to use a large amount of rinsing water.

If it is possible to prevent liquid from flowing from the nasal cavity to the throat heads, it would become possible to use an endoscope within a surgical viewing field filled with a water flow as in the case of an urethrae operation through urea in the field of urinary organs, also in the case of the nose surgical operation using an endoscope. This would enable prevention of contamination of the tip of the endoscope, removal of continuous blood, use of a great amount of rinsing water after the operation and prevention of bleeding inside the nasal cavity during the operation from flowing into the throat heads; however, conventional techniques have failed to achieve these functions.

Conventionally, with respect to items for preventing a liquid from flowing from the nasal cavity to the throat heads, for example, there have been provided Belloc* pads used for stopping nose bleeding and rear-nostril balloons for stopping nose bleeding. In the case of Belloc* pads, a pad, formed by compressing cotton or gauze, etc., is pull from the front-nostril side so as to press and close a rear nostril from the throat heads side; however, the pad is made of a fabric material, with the result that it fails to completely block a fluid from flowing inside. Moreover, the rear-nostril balloon for stopping nose bleeding has a structure in which the pad portion of the Belloc* pad is replaced by a balloon, and is used to press and close the rear nostril from the throat heads side in the same method; however, it has been found that, although the balloon has a high inner pressure at the time of application so that it has a sufficient fixing property, it fails to conform to the complex shape of the rear-nostril because of its lack of flexibility, resulting in a gap mainly on throat head side of the rear-nostril and serious degradation in the blocking property.

Moreover, there has been provided a yarmic* catheter in which the front-nostril and the rear-nostril are closed by respective balloons, and suction is applied thereto; however, it has been found that, although this achieves its main purpose that a negative pressure is applied with the air being blocked, it is not capable of providing a completely blocking property upon application of a great amount of water under a positive pressure.

SUMMARY OF THE INVENTION

The present invention has been devised to solve the above-mentioned problems and its objective is to provide a surgical balloon which can close a rear-nostril with a complete air-shielding property to prevent a liquid from flowing into throat heads independent of differences in the physique of a patient, even when a large amount of rinsing water is rapidly poured into a nasal cavity.

In other words, the present invention provides a surgical balloon which prevents a liquid or a gas from flowing from one area of the body to another area thereof by using an aggregate of a plurality of balloons, and this balloon has a structure in which one or a plurality of balloons are placed inside or outside of one or a plurality of balloons so that it simultaneously satisfies the fixing property and the shielding property.

The combination of a balloon having a fixing property and a balloon having a shielding property makes it possible to effectively prevent a liquid from flowing from a nasal cavity to throat heads. Therefore, since a surgical operation can be carried out with the nasal cavity being filled with a water flow, it is possible to prevent contamination to the tip of an endoscope, to continuously remove blood, and also to discharge a mucous membrane taken by forceps through the water flow; thus, it becomes possible to effectively carry out the surgical operation. Moreover, since the nasal cavity is filled with a water flow, an ultrasonic wave can be applied to the nasal cavity so that a medical examination can be carried out on the peripheral conditions of a surgical portion; thus, it is possible to prevent adverse effects from being given to an eye socket, optic nerves and cranium ground that are susceptible to accidents. Furthermore, the application of a strong rinsing process after the surgical operation makes it possible to prevent any infection after the surgical operation, and since leaving the balloon after the surgical operation makes it possible to stop bleeding, the patient is allowed to leave the hospital earlier.

In addition, it is possible to easily stop bleeding even in the case of a patient having a serious nose bleeding.

BRIEF DESCRIPTION OF THE DRAWINGS

FIG. 8 is viewed from below.

FIG. 11 is viewed diagonally from front.

FIG. 14 is viewed from below.

FIG. 16 is viewed from below.

FIG. 24 is viewed from the tip of an endoscope.

FIG. 27 is viewed in the direction of the tip of the endoscope.

DETAILED DESCRIPTION OF THE INVENTION

Figure 1:
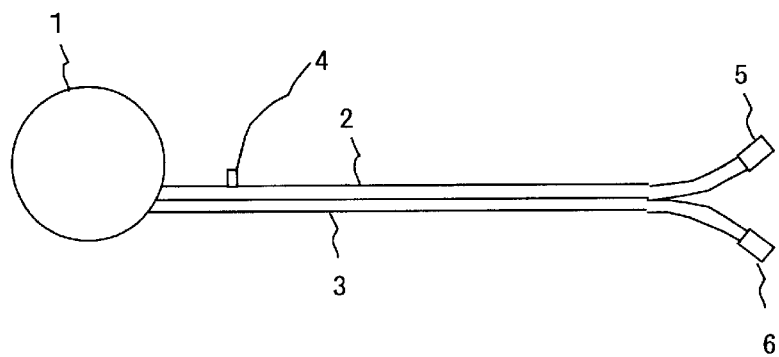
FIG. 1 is a plan view showing a surgical balloon in accordance with one example of the present invention.

A balloon used in the present invention is allowed to simultaneously satisfy a fixing property and a shielding property. For this reason, a surgical balloon, in which an aggregate of a plurality of balloons is utilized to prevent a liquid or a gas from flowing from one area of the body to another area thereof, is adopted. This balloon is provided with one or a plurality of balloons placed inside or outside of one or a plurality of balloons, and some of these balloons are allowed to have a fixing property and the others are allowed to have a shielding property so that the balloon as a whole can simultaneously satisfy the fixing property and the shielding property as a whole. In this case, the fixing property is exerted by those balloons having a high inner pressure and the shielding property is exerted by those balloons having a low inner pressure.

At this time, in the case when balloon inflating tubes are respectively connected to the balloons, air is injected into the respective balloons so as to inflate them independently.

In this case, among the balloons, one portion or the entire portions of the fixing balloons and one portion or the entire portions of the shielding balloons may have an air permeability; thus, the corresponding balloons have the same inner pressure so that it becomes possible to conform to a complex shape. In other words, the fixing balloons having a predetermined air permeability have the same inner pressure, and the shielding balloons having a predetermined air permeability have the same inner pressure; thus, uniform fixing effect and shielding effect of the balloons are obtained without being biased on one direction.

Moreover, a plurality of balloons are bonded to each other so as to be maintained in proximate positions so that it is possible to obtain stable balloon fixing and shielding properties.

In this case, when the lower side (throat heads side) of the shielding balloon is bonded to the fixing balloon, the shielding balloon is allowed to expand toward the head side of the rear-nostril that is more likely to have gaps, and also to expand toward the throat heads side, thereby preventing the respiratory tract from clogging.

Therefore, the up and down direction of the surgical balloons is essential; and there is preferably provided an expanding tube one portion of which bears a mark indicating the direction, or a protrusion for indicating the direction and for making the tube easier in handling at the time of the balloon insertion. Thus, the balloon can be inserted in an accurate direction.

The surgical balloon having the above-mentioned arrangement makes it possible to provide high degrees of fixing property and shielding property, which have not been achieved by a conventional single balloon, also to block liquid permeation between the nasal cavity and the throat heads.

The surgical balloon is inserted from the front nostril, and at a position where it enters the throat heads side from the rear nostril, the fixing balloon is expanded so that it is allowed to pull the balloon expanding tube from the front nostril; thus, the fixing balloon presses the rear nostril from the throat heads side. The fixing balloon, which has a hard characteristic as in the case of a conventional rear nostril balloon, is positively engaged mainly by the rear edge of the nostril partition* so that it would not be pulled out forwardly from the rear nostril even with a strong force. However, since the fixing balloon lacks flexibility, a gap is formed mainly on the head side of the rear nostril. Therefore, the shielding balloon is expanded so that it softly presses the surface of the rear nostril, thereby exerting a strong shielding effect. Moreover, since the shielding balloon is secured to the fixing balloon directly or indirectly, it is held at a stable position even in the case of violent movements on the periphery of the rear nostril due to swallowing movements and vocalization movements during a surgical operation.

Here, the shielding balloon mainly contacting the nasal cavity mucous membrane is flexible so that the patient is less susceptible to pain. With respect to the fixing process of the balloon, a conventional rear nostril balloon for stopping nose bleeding is fixed by pulling the balloon at the rear nostril by a tube-shaped member that is cut into and fixed onto the front nostril. However, since the member that is cut into and fixed onto the front nostril closes the front nostril, it is impossible to maintain a viewing field from the front nostril during the operation, making it impossible to carry out the surgical operation.

Moreover, a window-opening device, which opens the front nostril from inside to maintain the viewing field, has been conventionally used; however, it is impossible to use this to maintain the position against an expanding force from the rear nostril side.

In the present invention, in order to fix the surgical balloon while being pulled from the front nostril side, any one of the following devices is used: a surgical balloon fixing device for maintaining the position by covering one portion of the face; a front nostril window-opening device which presses the front nostril from inside so as to fix the position against the expanding force from the rear nostril, while maintaining a viewing field during the operation from the front nostril side; and a surgical balloon fixing device in which the front nostril window-opening device is installed.

The surgical balloon fixing device is allowed to contact a wide area including the cheek portions, nose side portions and philtrum so that an applied force is dispersed; the flat faces of these face portions are virtually perpendicular to a line connecting the front nostril and the rear nostril; and a portion at which the fixing member pinches the expanding tube is located in the center of the surgical balloon fixing device so that it is possible to maintain the balance of forces; thus, these factors make it possible to fix the surgical balloon in a very stable state, and also to simultaneously obtain a proper viewing field during the operation.

With respect to the water supplying methods, conventionally, water-supplying tubes of a bladder endoscope in which a large amount of rinsing water is sent to the tip of the endoscope and a nose endoscope in which a slight amount of anti-fogging liquid is sent to the tip of the endoscope have been proposed; however, both of these are hard, and less movable. A tube having a large diameter is required so as to send a large amount of rinsing water, and in the case when a conventional tube that is hard and less movable is used, mainly because the front nostril is narrow, the handling of surgical forceps is interrupted.

For this reason, it is preferable to use a flexible tube that is freely deformed so as not to interrupt the surgical operation as the tube for sending rinsing water into the nasal cavity. Moreover, when this tube is secured to a plane perpendicular to the major axis of the endoscope while maintained in a flexible state, it becomes possible to prevent this from interrupting various surgical operations.

Moreover, in order to supply a large amount of rinsing water into the nasal cavity without interrupting the operation viewing field from the front nostril side, a tube for sending rinsing water from the mouth cavity to the nasal cavity on the side opposite to the balloon expanding tube may be attached.

With respect to the draining method, a nose drain is held on the outside of the front nostril so that fluids coming from the front nostril are drained so that rinsing water, supplied into the nasal cavity, is continuously drained in a passive manner.

When the surgical balloon is fixed, the surgical balloon fixing device is pulled from the inside of the nose so that the nose drain is sandwiched between it and the face, thereby preventing the drain water from leaking. This arrangement makes it possible to carry out continuous draining, to avoid applying an excessive force onto the operation field, in a manner different from the bladder surgical operation using an endoscope, and to prevent the draining path from clogging, in a manner different from the draining process using a suction tube.

Referring to Figures, the following description will discuss examples of the present invention. However, the present invention is not intended to be limited thereby.

EXAMPLE 1

Figure 2:
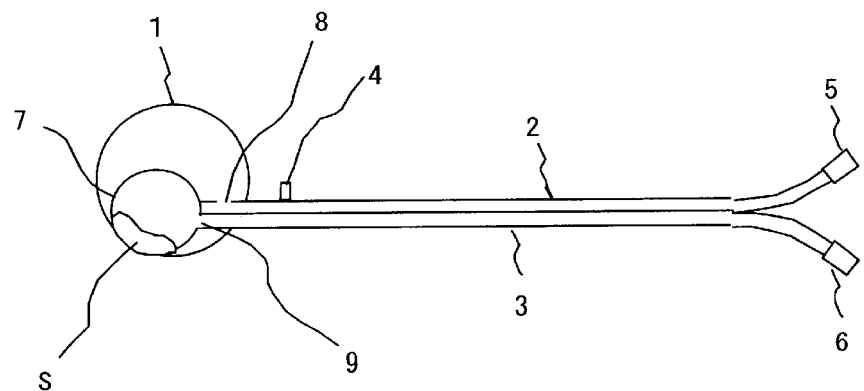
FIG. 2 is a side cross-sectional view of FIG. 1.
Figure 3:
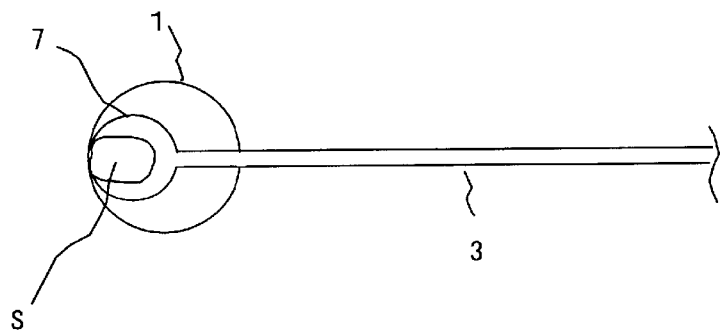
FIG. 3 is a cross-sectional view that shows a lower portion of FIG. 2 (one part of which is omitted).

FIG. 1 is a plan view that shows a surgical balloon in accordance with one example of the present invention, and FIG. 2 is a cross-sectional view obtained when the surgical balloon portion of FIG. 1 is viewed sideways. FIG. 3 is a cross-sectional view obtained when the surgical balloon of FIG. 1 is viewed from below (one portion of which is omitted). A first balloon 1, which is a rubber elastic member, is not particularly limited, and is formed into a spherical shape by using, for example, natural rubber, synthetic rubber such as isoprene rubber, silicone rubber, urethane rubber and ethylene-propylene rubber, and other elastomer. Here, it is preferable to use a material as thin as, and as flexible as a condom, and approximately 20 ml of air is injected thereto so as to provide an inner pressure of 10 cm/$H_2O$, or less.

A second balloon 7, which is a rubber elastic member, is not particularly limited, and is formed into a spherical shape by using, for example, natural rubber, synthetic rubber such as isoprene rubber, silicone rubber, urethane rubber and ethylene-propylene rubber, and other elastomers. Here, it is preferable to set the volume thereof to sufficiently as small as less than 1 ml without air inside thereof, and also to set the surface area to approximately 1 $cm^2$, and upon application, approximately 10 ml of air is injected so as to provide an inner pressure of approximately 20 cm/$H_2O$, or preferably greater. The second balloon 7 is placed inside of the first balloon 1, and the first balloon 1 and the second balloon 7 are directly bonded to each other at a contact portion S, or respective expanding tubes 2 and 3 are bonded to each other so that the first balloon 1 and the second balloon 7 are placed adjacent to each other.

For this reason, when the second balloon has been fixed to the rear nostril, the first balloon is also fixed indirectly so that it presses the periphery of the rear nostril with its flexible property. In other words, the second balloon is allowed to exert a fixing property with its high inner pressure, while the first balloon is allowed to exert its shielding property with its flexible property. The first balloon 1 and the second balloon 7 are formed so that air is independently injected thereto respectively from an expanding tube 2 and an expanding tube 3 through holes 8 and 9 via air inlets 5 and 6. Upon application, the first balloon 1 and the second balloon 7 without air inside therein are inserted through the front nostril while confirming the direction of a mark or a protrusion 4, and when located at a position where it enters the throat heads side from the rear nostril, approximately 10 ml of air is injected into the second balloon 7, and the expanding tubes 2 and 3 are pulled from the front nostril so as to confirm that the second balloon 7 has been engaged by the rear nostril; thus, while being pulled, approximately 10 ml of air is injected into the first balloon 1 so that the expanding tubes 2 and 3 are secured to the surgical balloon fixing device.

Since the first balloon is bonded to the second balloon on the lower side, it is allowed to expand toward the head side of the rear-nostril that is more likely to have gaps to exert its efficient shielding property, and also to expand toward the throat heads side, thereby preventing the respiratory tract from clogging.

Figure 4:
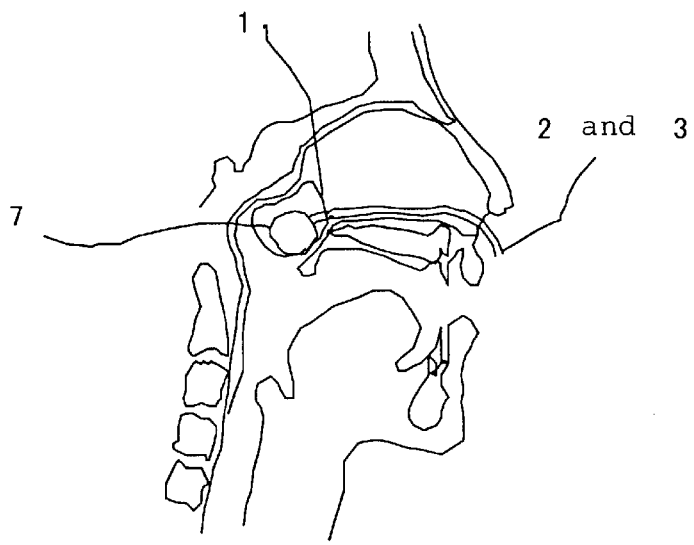
FIG. 4 is an explanatory drawing that shows a state in which the surgical balloon of the present invention is used.

FIG. 4 is a drawing that explains an applied state of the surgical balloon of the present invention.

Figure 5:
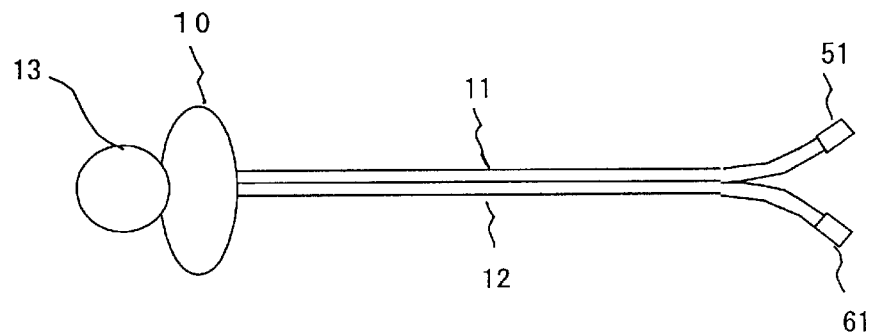
FIG. 5 is a plan view that shows another example of the surgical balloon of the present invention.
Figure 6:
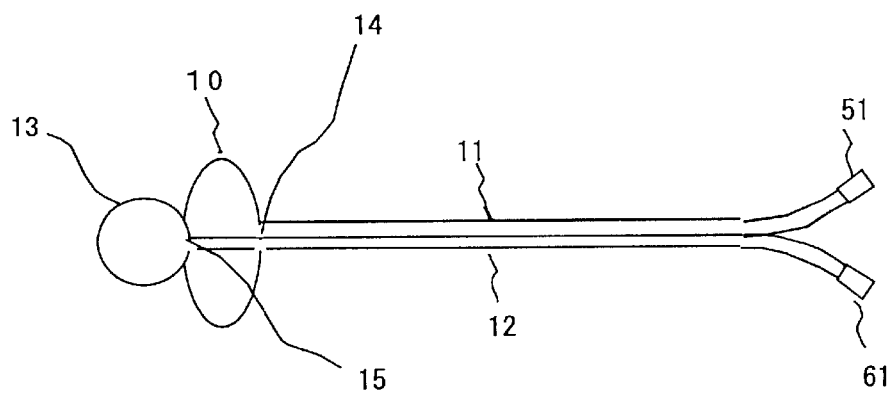
FIG. 6 is a cross-sectional view of FIG. 5.
Figure 7:
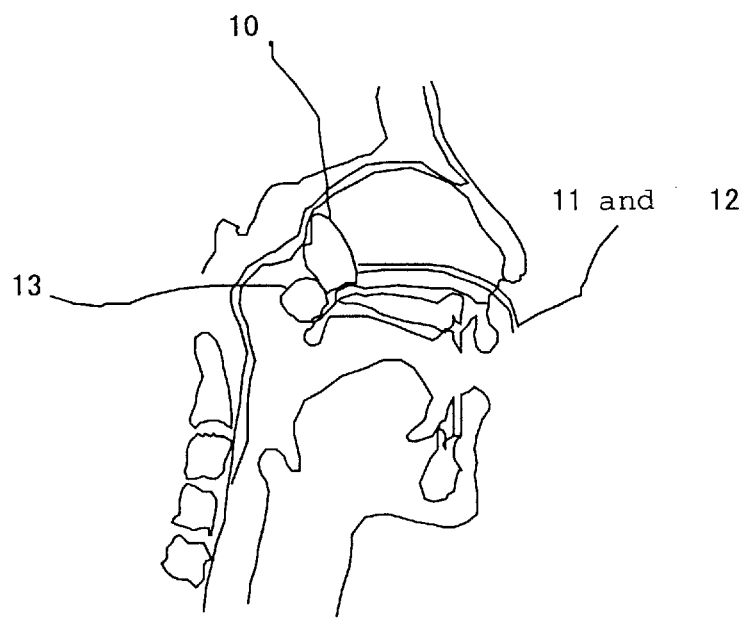
FIG. 7 is an explanatory drawing that shows a state in which the surgical balloon of the present invention, shown in FIGS. 5 and 6, is used.

FIG. 5 is a plan view that shows a surgical balloon in accordance with another example of the present invention. FIG. 6 is a cross-sectional view thereof. This example is different from the example shown in FIGS. 1, 2, 3 and 4 in that the second balloon is placed on the external tip side of the first balloon; however, the material is the same, and a second balloon 13 is allowed to exert a fixing property by pressing and closing the rear nostril from the throat heads side, and a first balloon 10 is allowed to exert a shielding property by injecting air independently through holes 15 and 14 from air inlets 61 and 51 via expanding tubes 12 and 11. The first balloon 10 is held at a position adjacent to the second balloon 13 so that it is allowed to exert a fixing property indirectly. FIG. 7 is a drawing that explains an applied state of the surgical balloon of the present invention of the example shown in FIGS. 5 and 6.

Figure 8:
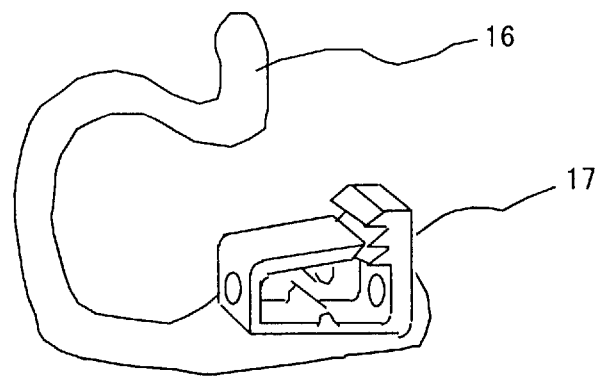
FIG. 8 is a plan view that shows a left-nostril-use surgical balloon fixing device in accordance with one example of the present invention, when viewed from the lower front side.
Figure 9:
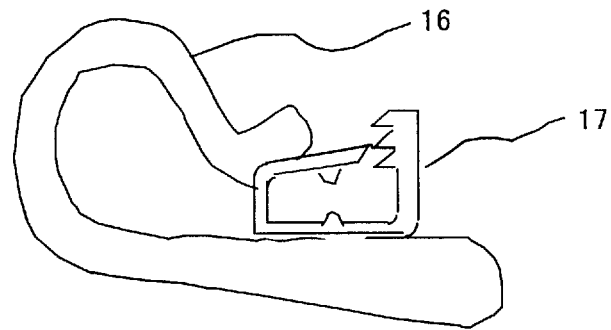
FIG. 9 is a drawing obtained when

FIG. 8 is a plan view that shows a surgical balloon fixing device in accordance with one example of the present invention, which is obtained when viewed from slightly below on the front side. FIG. 9 is a drawing that is obtained when FIG. 8 is viewed from below. The material of a fixing device main body 16 is not particularly limited by plastics and metals, and may have slight flexibility as long as it has a sufficient hardness to support the expanding force of the expanding tubes 2, 3, 11 and 12. In particular, a portion thereof, which is to contact the skin, is preferably covered with a flexible material such as rubber.

The fixing device main body 16 is maintained stably by covering an area of the face including the cheek portions, nose side portions and philtrum, while a fixing member 17, bonded and fixed to the fixing device main body 16, is pulling the balloon expanding tubes 2, 3, 11 and 12 to fix them in a sandwiched state.

With respect to the fixing device 17, any method may be used as long as it fixes the expanding tubes 2, 3, 11 and 12 in a sandwiched state. The fixing device 17, shown in FIGS. 8 and 9, is actually used as a plastic device for sandwiching and fixing the tubes; and for example, the same device is used as a device for adjusting the liquid of a tube that drains rinsing liquid during a bladder surgical operation using an endoscope.

Figure 10:
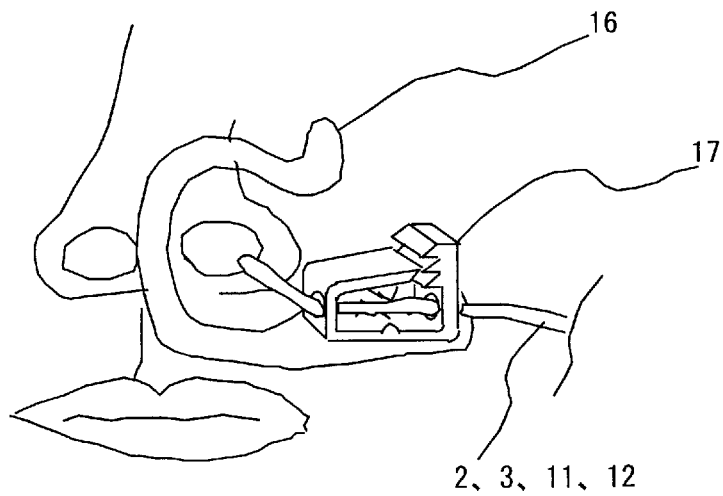
FIG. 10 is an explanatory drawing that shows a state in which the left-nostril-use surgical balloon fixing device of the present invention is used.

FIG. 10 is an explanatory drawing that shows a state in which the surgical balloon fixing device of the present invention is used. The balloon expanding tubes 2, 3, 11 and 12, extended from the front nostril, are fixed by the fixing device 17 while being pulled.

Figure 11:
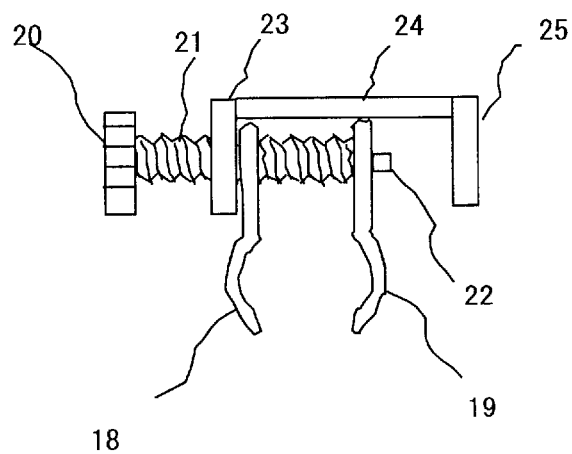
FIG. 11 is a front view that shows a front-nostril window-opening device used in another example of the surgical balloon of the present invention.
Figure 12:
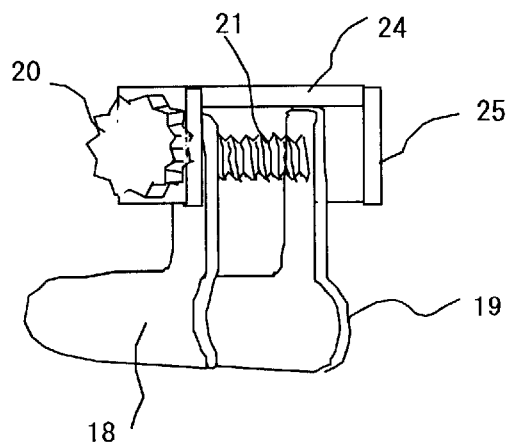
FIG. 12 is a drawing obtained when

FIG. 11 is a front plan view of a front nostril window-opening device N in accordance with one example of the present invention, and FIG. 12 is a drawing that is obtained when FIG. 11 is viewed diagonally from the front side. Here, a handle 20, a threaded portion 21 and a fastening member 22 are bonded and fixed thereto, and when the handle 20 is rotated, a front nostril left-side insertion section 19, sandwiched between the threaded portion 21 and the fastening member 22, is moved along a frame upper portion 24 in parallel therewith. Since a frame right portion 23 and a front nostril right-side insertion section 18 are bonded and fixed, the rotation of the handle 20 makes it possible to change the distance between the front nostril left-side insertion section 19 and the front nostril right-side insertion section 18 so that the front nostril is pressed from the inside so as to be widened.

The frame left portion 25 is bonded and fixed to the frame upper portion 24.

Figure 13:
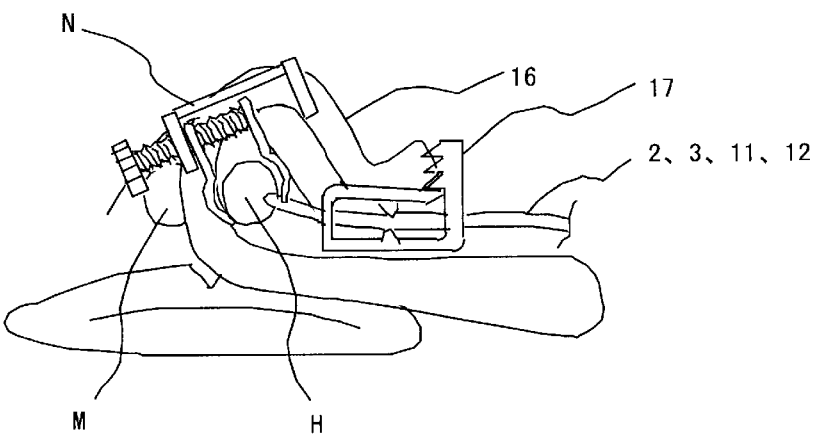
FIG. 13 is a drawing viewed from below that explains a state in which the surgical balloon fixing device (left-nostril-use) of another example of the present invention to which the front-nostril opening device shown in FIGS. 11 and 12 is attached is used.

FIG. 13 is a drawing viewed from below that explains a surgical balloon fixing device of another example formed by attaching the front-nostril window-opening device N shown in FIGS. 11 and 12 to the surgical balloon fixing device shown in FIGS. 8, 9 and 10. The front-nostril window-opening device N that presses the left front nostril H from the inside thereof is attached so that the front nostril is held in a stable position, and the front nostril is widened to provide a wider surgical field.

Figure 14:
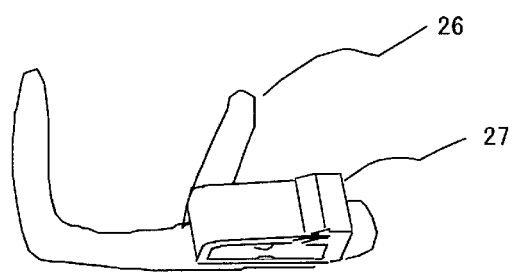
FIG. 14 is a drawing that shows a surgical balloon fixing device (left-nostril-use) in accordance with another example of the present invention, when viewed from the lower front side.
Figure 15:
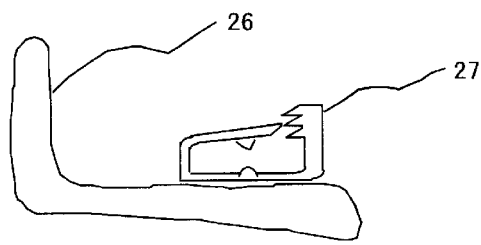
FIG. 15 is a drawing obtained when

Here, since the right front nostril M, which is not on the operation side, is opened, breathing is available. FIG. 14 is a plan view that shows a surgical balloon fixing device in accordance with another example of the present invention, when viewed from the lower front side. FIG. 15 is a drawing that is obtained when FIG. 14 is viewed from below.

In the same manner as the example shown in FIGS. 8, 9, 10 and 13, a fixing device main body 26 is maintained stable by covering an area of the face including the cheek portions, nose side portions and philtrum, while a fixing member 27, bonded and fixed to the fixing device main body 26, is pulling the balloon expanding tubes 2, 3, 11 and 12 to fix them in a sandwiched state.

Figure 16:
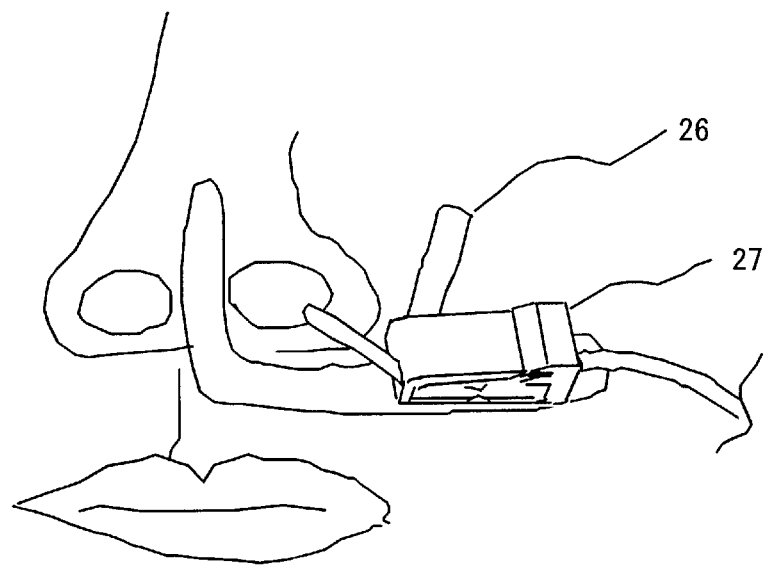
FIG. 16 is an explanatory drawing that shows a state in which the surgical balloon fixing device shown in FIGS. 14 and 15 is used.
Figure 17:
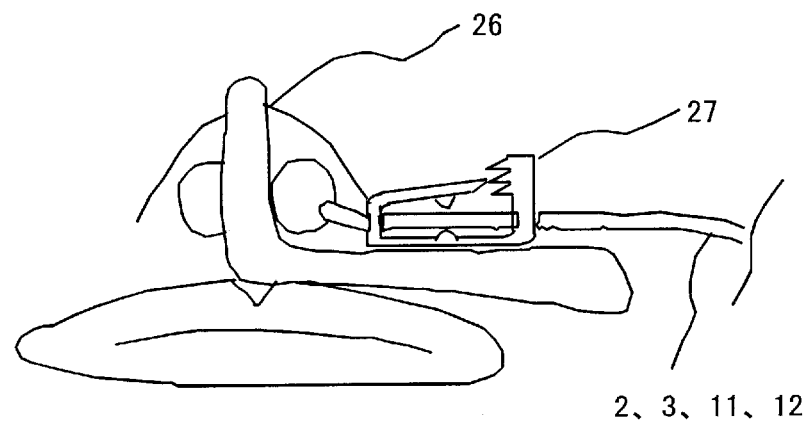
FIG. 17 is a drawing obtained when

FIG. 16 is an explanatory drawing viewed from slightly below on the front side that shows a state in which the surgical balloon fixing device of the present invention shown in FIGS. 14 and 15 is used. FIG. 17 is a drawing obtained when FIG. 16 is viewed from below.

Figure 18:
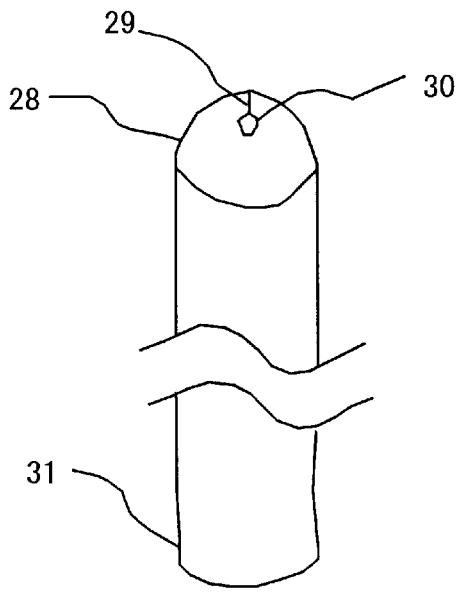
FIG. 18 is a plan view showing a nostril drain in accordance with one example of the present invention.

FIG. 18 is a plan view that shows a nose drain in accordance with one example of the present invention. The material for this is not particularly limited as long as it is a thin material such as a vinyl sheet with a water-proof property. It is a tube with opened ends having a diameter of approximately 10 cm and a length of approximately 1 m, and designed to be shorter on a semi-circumferential portion of the nose side end 28 (on the front side) so as to maintain a proper surgical viewing field, while the other semi-circumferential portion is designed to be longer so as to be sandwiched between the skin on the periphery of the front nostril and the surgical balloon fixing device, with an insertion-use slot 29 and a front-nostril-use hole 30 used for viewing the front nostril being formed therein.

Figure 19:
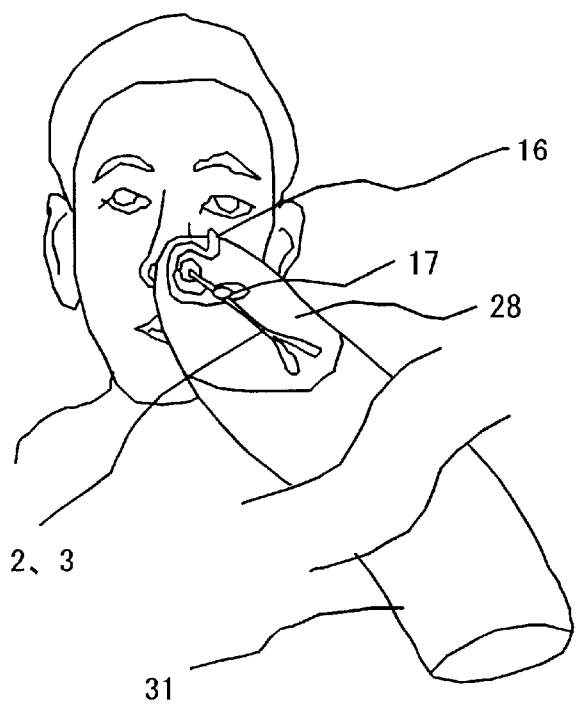
FIG. 19 is an explanatory drawing that shows a state in which the nostril drain of the present invention is used.

FIG. 19 is a drawing that explains a state in which the nose drain of the present invention is used.

When the expanding tubes 2, 3, 11 and 12 of the surgical balloon are sandwiched by the fixing member 17 of the surgical balloon fixing device, the surgical balloon fixing device is pulled toward the front nostril side to press the face so that in the case when the nose side end 28 is sandwiched between the skin on the periphery of the front nostril and the surgical balloon fixing device, the nose drain is fixed to prevent drain water from leaking. A drain end 31 of the nose drain is connected to a drain container.

Figure 20:
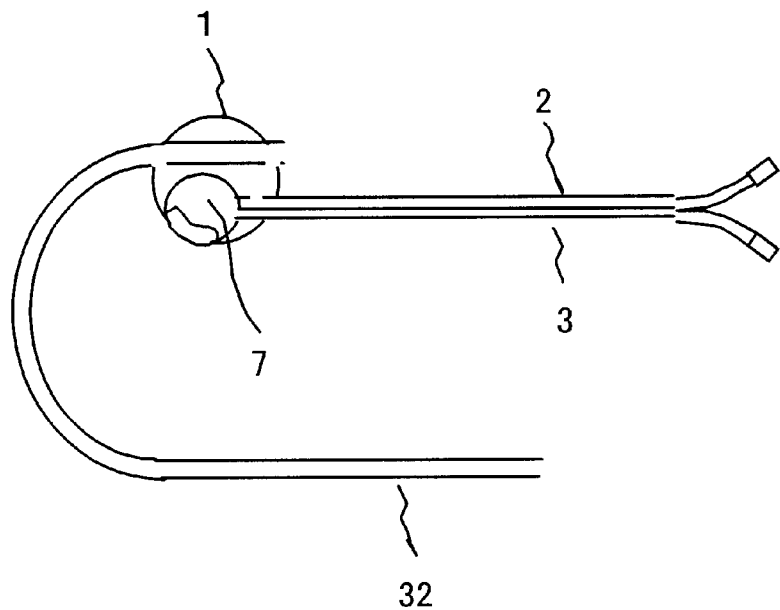
FIG. 20 is a cross-sectional view that shows another example of the surgical balloon of the present invention in which a water-supplying tube is placed from the mouth cavity side.

In general, the front nostril is narrow with the result that it is difficult to provide a sufficient surgical field, while a water supplying tube having a large diameter needs to be placed so as to supply a large amount of rinsing water, which is a contradictory situation. In order to solve this problem, any one of the following tubes is used to supply rinsing water: a tube that reaches the inside of the nose by penetrating the balloon from the mouse cavity side; a tube that is formed by a soft material such as vinyl into a bag-shape covering an endoscope, or is freely deformed along the side of the endoscope so as not to interrupt the surgical operation; and a tube that is fixed flexibly on a plane perpendicular to the major axis of the endoscope so that it is allowed to freely move in response to the surgical operation. FIG. 20 is a cross-sectional view showing still another example of a surgical balloon which is formed by attaching a water supplying tube that reaches the other side from the side opposite to the expanding tubes 2 and 3 by penetrating the first balloon 1 so as to supply rinsing water from the mouth cavity side to the nasal cavity side to the surgical balloon shown in FIGS. 1, 2, 3 and 4 of the example of the present invention.

Figure 21:
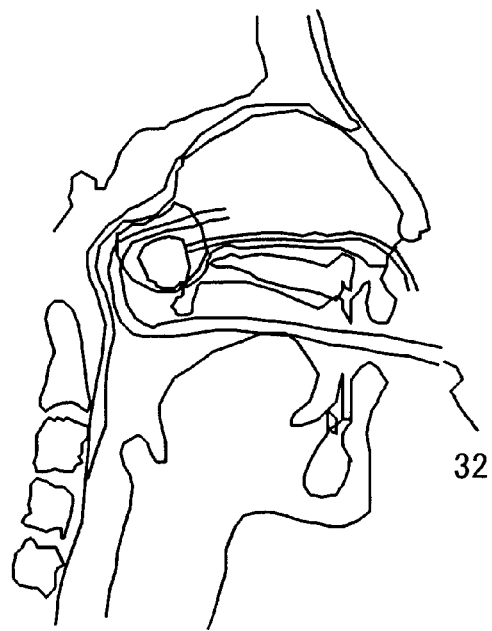
FIG. 21 is a drawing that explains a state in which the surgical balloon in which a water-supplying tube is placed from the mouth cavity side, as shown in FIG. 20, is used.

FIG. 21 is a drawing that shows a state in which the surgical balloon shown in FIG. 20 is actually applied.

Figure 22:
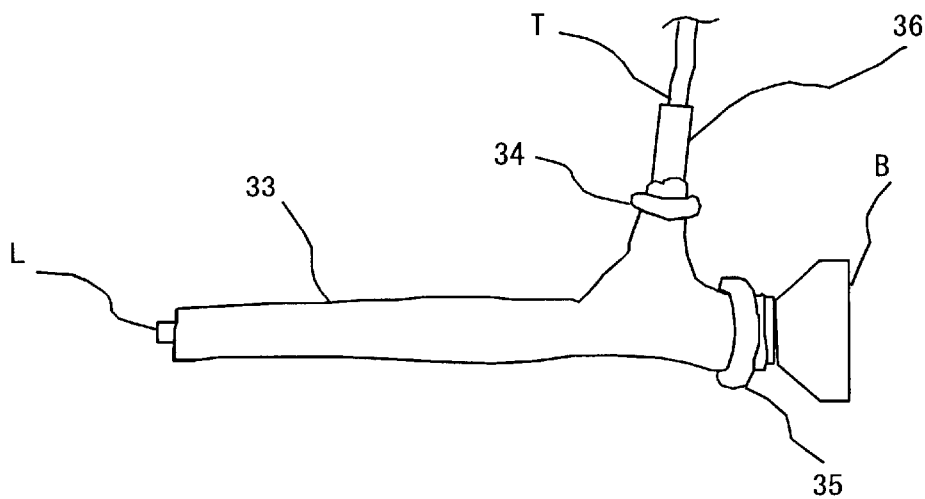
FIG. 22 is a plan view that shows one example of a soft nasal water-supplying tube of the present invention.
Figure 23:
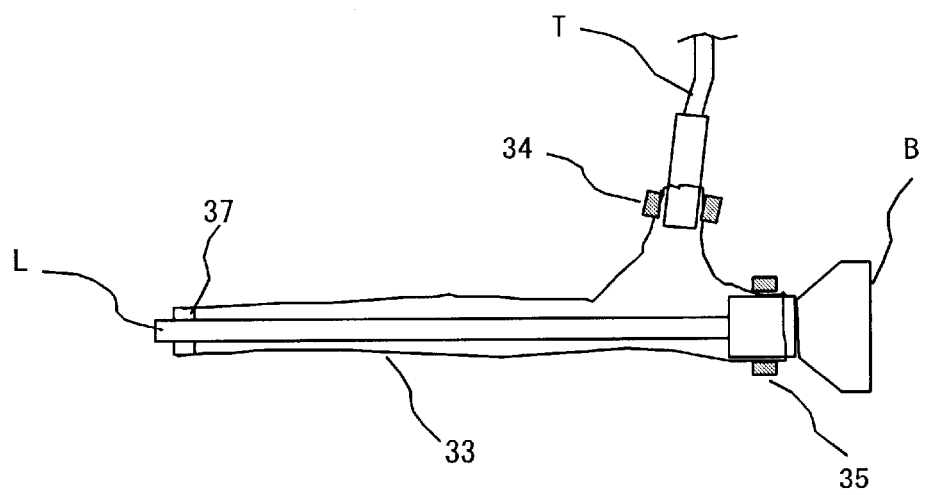
FIG. 23 is a cross-sectional view of FIG. 22.

FIG. 22 is a plan view that shows a soft nose water-supplying tube in accordance with one example of the present invention, and FIG. 23 is a cross-sectional view of FIG. 22. A soft tube main body 33 is formed by any material as long as it is a soft, thin material such as vinyl having a water-proof property, and has a bag-shape covering an endoscope; however, a portion thereof at which the tip of the endoscope L, the base B of the endoscope and a tube T through which rinsing water is supplied, or a connector 36 thereof, are connected is in an opened state. The base B of the endoscope and the tube T through which rinsing water is supplied are pressed and fixed by rubber rings 35 and 34 so as to prevent water from leaking.

Figure 24:
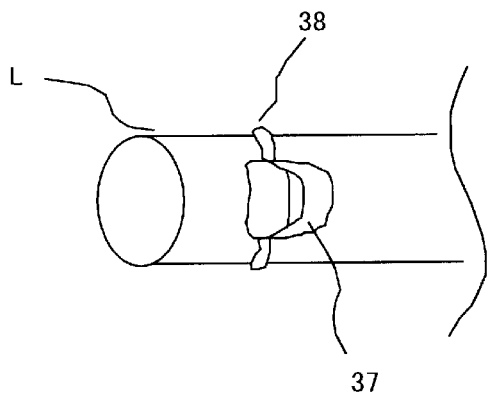
FIG. 24 is a perspective view of FIGS. 22 and 23 (one portion of which is omitted), wherein a soft tube main portion 33 is omitted.
Figure 25:
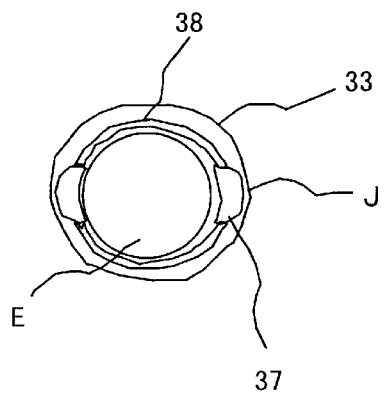
FIG. 25 is a drawing obtained when

FIG. 24 is a perspective view that shows the tip of the soft nose water-supplying tube of FIG. 24 (from which the soft tube main body 33 is omitted). With respect to an opening device 37, any material may be used as long as it is a thin, flexible material such as vinyl. A line rubber 38 is connected to the opening device 37 to form a ring, and this is wound around an endoscope and attached thereon. FIG. 25 is a drawing obtained when FIG. 24 is viewed from the tip side of the endoscope. The soft tube main body 33 is bonded to the opening device 37 at a bonding portion J. The tip side of the endoscope E forms an open end from which water is discharged with the result that it is not necessary to provide an air-sealing property and it is only necessary to fix this so as not to be offset in its position.

Figure 26:
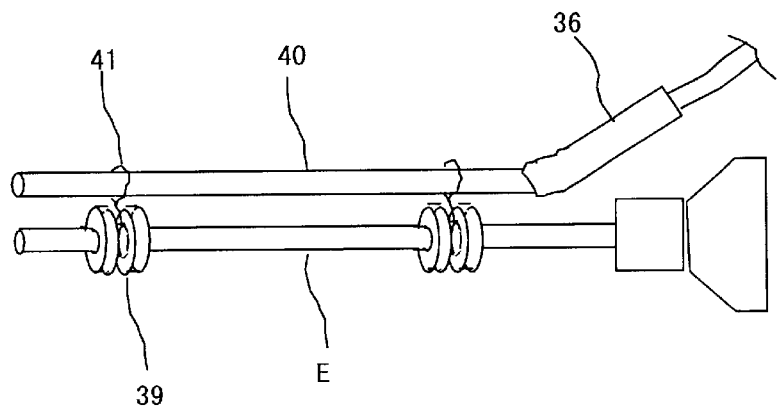
FIG. 26 is a plan view that shows one example of a movable nasal water-supplying tube of the present invention.
Figure 27:
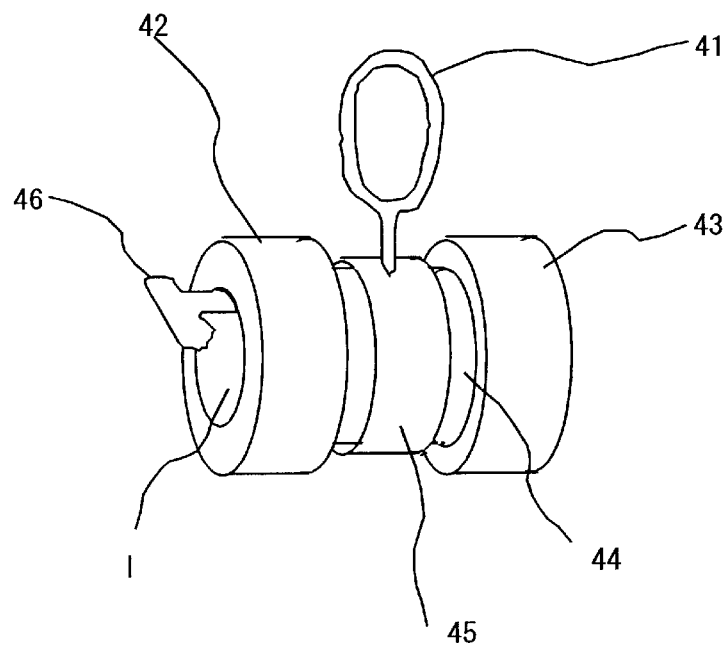
FIG. 27 is a perspective view of a fixing section 39 of FIG. 26.

FIG. 26 is a plan view that shows a movable nose water-supplying tube in accordance with one example of the present invention. FIG. 27 is a perspective view showing a mounting device 39 in FIG. 26. The mounting device 39 whose material is not particularly limited and is a material such as plastic and rubber is constituted by flange portions 42 and 43 and a cylinder body 44, and an inner cavity I in which the endoscope E is inserted is provided therein. A ring-shaped movable ring, which is allowed to move freely, is placed on the cylinder body 44 sandwiched by the flanges 42 and 43, and a rubber ring 41 is attached thereto. After having been attached to the endoscope E, the mounting device 39 is fixed by winding a small rubber ring around a rubber-ring-use protrusion 46, or the mounting device 39 itself is formed as a rubber elastic member so that it is fixed onto the endoscope through an elastic force. A water supplying tube 40 is inserted to the rubber ring 41 so that the water supplying tube 40 is regulated in its movement in the major-axis direction of the endoscope; however, it is allowed to move in the rotation direction of the movable ring 45 so that it is shifted to a position so as not to interrupt various operations during the surgical operation.

Figure 28:
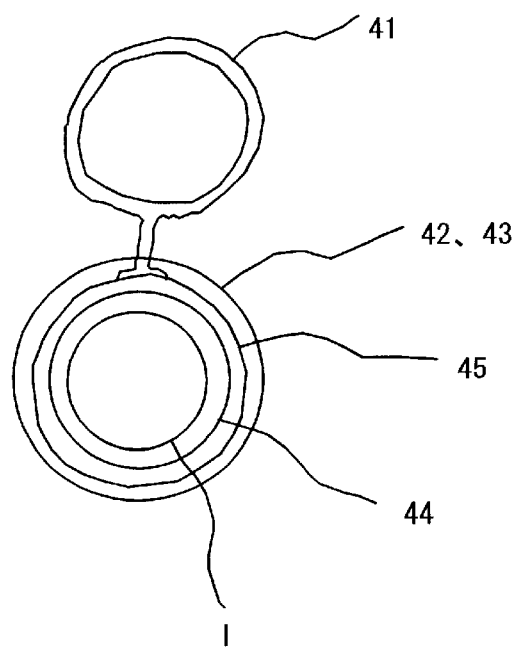
FIG. 28 is a drawing obtained when

FIG. 28 is a drawing obtained when FIG. 28 is viewed from the endoscope tip side. The water supplying tube 40 is preferably set to have a diameter not more than 5 mm, and the material thereof is not particularly limited, and is made of thin plastic, etc.

EXAMPLE 2

The surgical balloon, produced in accordance with example 1, was used in a nose surgical operation using an endoscope. As a result, it became possible to carry out the operation while supplying a large amount of rinsing water rapidly. Even in the case when 1000 ml of physiological salt solution was flown in one minute, no liquid was allowed to leak into the throat heads so that it was possible to carry out the surgical operation safely. Solidified blood on the surgical field was completely washed, and a clear viewing field of the nasal cavity in water which had not been experienced was obtained.

Moreover, by applying the surgical balloon and the surgical balloon fixing device, the patient was free from a pain.

Furthermore, it became possible to use diagnosing ultrasonic waves inside the nasal cavity filled with water, which had not been applied to a nose surgical operation using an endoscope since it was not used in the air; thus, it became possible to insert a ultrasonic wave fine-diameter probe, and consequently to obtain a ultrasonic wave image of the inside of the nasal cavity on the periphery of the surgical portion. In the inner nose surgical operation, conventionally, it might cause a serious accident such as loss of sight due to a damage to an eye nerve or leakage of marrow liquid due to a damage to a dura mater; however, it became possible to confirm such damage-prone parts beforehand.

EXAMPLE 3

Conventionally, there has been a problem in which a serious infection might occur after the surgical operation since it has been difficult to carry out rinsing and disinfecting operations after the nose surgical operation using an endoscope. However, in 43 cases in which strong rinsing and disinfecting operation were carried out by using the surgical balloon, no infection after the surgical operation was experienced.

EXAMPLE 4

By leaving the surgical balloon after the surgical operation, it became possible to completely prevent bleeding after the operation. Since bleeding after the operation might cause a danger in life, it had been necessary for the patient to be hospitalized for a week; however, it became possible to leave the hospital the day after the operation.

EXAMPLE 5

With respect to an example other than the operation, the surgical balloon was applied to a patient suffering from a serious nose bleeding that could not be stopped by Belloc* pads, and it was possible to completely stop the bleeding by using a much simpler method as compared with Belloc* pads. Moreover, the Belloc* pads tend to cause serious complications since they press the mucous membrane excessively; therefore, it is necessary to avoid leaving them for a long time. In contrast, the surgical balloon is allowed to contact the mucous membrane flexibly in a wider area so that no problem arises even after it has been left for a week.

EXAMPLE 6

There is a patient who suffers unpleasantness when a balloon for fixing is left at the throat heads towards a side of the rear-nostril to prevent a nose bleeding. Even if the use during the short time operation causes no problem, there is a case to cause pain if it is left for several days. The high inner pressure fixing balloon, which is the inside balloon is left at nasal cavity side from rear-nostril, and the shielding outside low pressure balloon which contains inner balloon is expanded in the nasal cavity. In this case, since the fixing balloon is engaged by the rear edge of ethoid, it can maintain the stable position by pulling out forwardly the balloon expanding tube from the front-nostril. This leaving method after operation is carried out to three patients, and the bleeding after operation can be stopped without accompanying unpleasantness. Compared with the method to leave the fixing balloon at the throat heads side of the rear-nostril, although this method does not have a strong shielding effect to reflux the inside of nasal cavity is by rinsing water, has a sufficient shielding effect to prevent bleeding after operation and has a strong point that of no accompanying unpleasantness.

EXAMPLE 7

The surgical balloon in which the high pressure inside balloon and surrounding low pressure outside balloon are not adhered is inserted into throat heads side of the rear-nostril and used for the nose endoscope operation. When rinsing water is poured into, the gap is remained at the upper side of rear-nostril, and in cases of three clients rinsing water is leaked into the throat heads. Since the lower part of rear-nostril is opening toward the throat heads, even if the outside balloon is expanded largely, the power is dispersed toward the throat heads, and does not act as the power to press the upper part of the rear-nostril. Therefore, it becomes clear that by adhering the lower surface of inside balloon and outside balloon, the outside balloon expands toward upper direction based on the inside balloon whose position is fixed and press the upper part of rear-nostril strongly so as the rear-nostril to be shielded effectively.

EXAMPLE 8

To drain the rinsing water poured into nasal cavity, a vacuum tube is inserted into the front-nasal cavity and water drained by continuous vacuum. When a thin tube is used, the large amount of drain is impossible, further, the removed tissue blocks the tube very often and the drain itself is stopped. To carry out the draining of high amount of water a thicker tube is needed, however, when a thicker tube is left at narrow front-nostril the operation itself is remarkably disturbed by it.

In 45 cases which receive the flown rinsing water from front-nostril at the outside of nose using a nose liquid drain, the draining liquid is not blocked and a stable continuous drain of liquid is possible, further there is no disturbing of the operation.

EXAMPLE 9

As the different type of fixing device different from the operation balloon fixing device, a balloon fixing device which is adhered on ridgeline of nose is prepared and tested. Since the balloon is engaged to the rear-nostril, the fixing device is pulled forward the rear-nostril side when fixed by pinching the tube for expansion. Therefore, the fixing device is pulled down from the ridgeline of the nose and stopped at the position to block the front-nostril. The part which pinches the tube for expansion is inserted into the nasal cavity and other part of the fixing device is floating in front of the face, and is impossible to maintain the adhered state of the ridgeline of the nose. The rear-nostril is remarkably deformed by pressing, and viewing field for operation is disturbed because the fixing device exists in front of the front-nostril, further, the fixing device floating in front of the face interrupting various surgical operations.

In the meanwhile, when the fixing device covering an area of the face including the area of the face, nose side portions and philtrum, which is the surgical balloon fixing device of the present invention, the position is not shifted because the surface is vertical to the direction pulled forward from rear-nostril side. Further, since the surface is supported by strong maxilla, the stable position can be maintained against the strong power pulled forward by the balloon. The balloon expanding tube is fixed by pinching the fixing part of the fixing device, and since the fixing part locates closely to cheek, the balloon expanding tube is pulled down to the downward of the front-nostril. Therefore, the balloon expanding tube does not disturb the viewing field for operation and enlarge the front-nostril, which is recognized as a strong point to extend the viewing field.

To fix rear-nostril balloon stable, it is necessary to against the strong power, and the conventional methods, for example, Belloc tampon, balloon for otorhinolaryngology (medical device approval No.16100BZZ01013000) or YAMIK catheter (PCT/SU89/00157) is characterized to close the front-nasal.

Therefore, up to the present, it is impossible to open the front-nostril at the operation.

By the fixing device of this invention, it becomes possible to dissolve two problems, that is, sufficient stability and maintaining viewing field of front-nasal at one time, because the fixing device of this invention utilizes the maxilla from philtrum to area of the face has sufficient strength and the surface is vertical to the line connecting rear-nostril and front-nostril.

EXAMPLE 10

A surgical balloon fixing device to which a front-nostril window-opening device is attached is used. As the conventional front-nostril window-opening device, JP-1016 Y2 (Tanaka Kunizo) (01.05.22) is already known. And by said device, it is possible to maintain the front-nostril open during the operation, but not measure to maintain the position against the strong power pulled forward from rear-nostril. It becomes clear that when the balloon is fixed using front-nostril window-opening device of this invention, the fixing power is dispersed to three components; the first one is the power of the fixing device to cover the face, the second one is the power of front-nostril window-opening device to oppress the front-nostril from inside and the third one is the power of front-nostril to cover and oppress the portion from the exit of the front-nostril to the outer surface of nose. Thus the balloon can be fixed tightly.

The area closed to the exit of front-nostril is depressed by the oppression of front-nostril window-opening device, however, the viewing field for operation become wider by oppressing from inside. Further, there is a strong point that the oppressing power added to face can be reduced, because the power can be effectively dispersed in comparison with the case that the surgical balloon fixing device to with front-nostril window opening device is not attached.

EXAMPLE 11

As the method to pour rinsing water using surgical balloon, the method to use an injection besides endoscope can be mentioned. However, for the purpose not only to rinse the inside of nasal cavity but also to carry out the operation under the water flow, which is the object of the surgical balloon of the present invention, it is necessary to take a measure that the rinsing water is spouted from the end point of endoscope and secure the viewing field for operation. This method is usually used in the endscope used at the transurethral operation of the urology. According to this method, blood or removed tissue in front of the endoscope are blown off from the view sight of the endoscope, further, it becomes possible to remove the stain stuck to the surface of lens and the viewing field become clear. However, in a transurethral operation of the urology, since the metallic path for rinsing water exists surrounding endoscope, the diameter of endoscope becomes thicker. The operation in nasal cavity is accompanied with bleeding, and in some case it is necessary to spout excessive rinsing water of 1000 ml/min from the end point of endoscope for the purpose to secure the clear view sight necessary to carry out the operation. In the meanwhile, if a rigid water supplying tube is arranged along with the endoscope which make the supplying of above mentioned excessive water possible, it disturbs the normal forceps action in a narrow nasal cavity. When a water supplying tube made from soft materials which is arranged along with the endoscope and opens at end point of endoscope, it can secure the water spouting of 1000 ml/min, and since it deforms flexibly to the forceps action, it is not an obstruction of the operation.

POSSIBILITY FOR THE INDUSTRIAL USE

As clearly shown by the above-mentioned description, the application of the surgical balloon of the present invention makes it possible to obtain the following effects.

The combination of a balloon having a fixing property and a balloon having a shielding property makes it possible to effectively prevent a liquid from flowing from a nasal cavity to throat heads. Therefore, since a surgical operation can be carried out with the nasal cavity being filled with a water flow, it is possible to prevent contamination to the tip of an endoscope, and consequently to omit processes for taking out the endoscope so as to be wiped. It is also possible to continuously remove blood, and also to discharge a mucous membrane taken by forceps through the water flow. Thus, it becomes possible to effectively carry out the surgical operation.

Since it is possible to prevent bleeding blood inside the nasal cavity from flowing into the throat heads, it becomes possible to avoid giving pain to the patient and danger of mis-swallowing.

Since the nasal cavity is filled with a water flow, an ultrasonic wave can be applied to the nasal cavity so that the positions of an eye socket, optic nerves and cranium ground that are susceptible to accidents during a nose surgical operation using an endoscope can be confirmed as images, it is possible to prevent damages due to the operation beforehand.

The application of a strong rinsing process after the surgical operation makes it possible to prevent any infection after the surgical operation. Since leaving the balloon after the surgical operation makes it possible to stop bleeding, the patient is allowed to leave the hospital earlier.

It is possible to easily stop bleeding for a long period even in the case of a patient having serious nose bleeding by using a simple operation.

What is claimed is:

1. A surgical balloon comprising, an aggregate of a plurality of balloons closely located with each other,
    wherein in order to close a space connecting one area in a body to another area thereof so as to block a liquid or a gas flowing through the space, at least one balloon is press-adhered to a portion adjacent to bone tissue, cartilage tissue or hard tissue so as to be fixed thereon while other balloons closely adjacent thereto are indirectly fixed and allowed to expand with the fixed position being maintained, so as to shield a peripheral area;
    wherein the aggregated balloons include balloons having a high inner pressure and balloons having a low inner pressure that are closely located with each other, the balloons having a high inner pressure being press-adhered and fixed onto a nasal cavity or a rear nostril with other balloons adjacent thereto being allowed to expand to block the nasal cavity and throat heads from communicating with each other
    wherein a shielding balloon having a low inner pressure contains a balloon inside having a high inner pressure while keeping a positional relationship with contact faces being maintained so that the shielding balloon having a low inner pressure, located outside, is allowed to expand in a direction opposite to the contact face with the fixed balloons having a high inner pressure, located inside thereof, thereby exerting a pressing force in a specific direction.

2. The surgical balloon according to claim 1, wherein a balloon having a high inner pressure is allowed to expand in the rear nostril on the throat heads side or the nasal cavity side so as to be held and fixed therein so that a balloon having a low pressure and containing the balloon having a high inner pressure is allowed to press a membrane located on the periphery thereof while maintaining a stable position at an area from the rear nostril to the nasal cavity.

3. The surgical balloon according to claim 2, which further comprises a tube that reaches the mouth cavity side from the nasal cavity by penetrating the balloon held at the rear nostril so that rinsing water is sent from the mouth cavity side into the nasal cavity or waste fluid is sent from the nasal cavity side to the mouth cavity side.

4. The surgical balloon according to claim 3, which further comprises a surgical balloon fixing device that forms a face virtually perpendicular to a direction connecting the rear nostril to the front nostril without interrupting surgical operations from the front nostril by covering a portion of a face from a philtrum to cheeks, so as to cope with a pulling force from the rear nostril, and that also fixes an expanding tube of the surgical balloon while pulling it from the rear nostril side to the front nostril side by attaching a fixing member for pinching and fixing the tube thereto.

5. The surgical balloon according to claim 1, which further comprises a surgical balloon fixing device that has a front nostril window-opening device which maintains a surgical viewing field by pressing the front nostril from the inside, and covers a portion from the periphery of the outlet of the front nostril to the outer surface of a nose so as to cope with a pulling force from the rear nostril, and that also fixes an expanding tube of the surgical balloon while pulling it from the rear nostril side to the front nostril side by attaching a fixing member for pinching and fixing the tube thereto.

6. The surgical balloon according to claim 5, which further comprises a nose drain that is held on the outside of the front nostril and attached to the face so that fluids coming from the front nostril are drained.

7. The surgical balloon according to claim 6, which further comprises a soft nose water-supplying tube that runs along an endoscope, and has an opening in the vicinity of the endoscope tip, and that is freely deformed so as not to interrupt a surgical operation, and supplies rising water to the nasal cavity.

8. The surgical balloon according to claim 1, which further comprises a movable nose water-supplying tube that is secured to an endoscope in a fixed manner in the major-axis direction of the endoscope and in a manner so as to move within a plane perpendicular to the major axis.

9. The surgical balloon according to claim 1, further comprising a plurality of said shielding balloons.

* * * * *